United States Patent
King et al.

(10) Patent No.: US 6,316,668 B1
(45) Date of Patent: *Nov. 13, 2001

(54) ACID SORPTION REGENERATION PROCESS USING CARBON DIOXIDE

(75) Inventors: C. Judson King, Kensington, CA (US); Scott M. Husson, Anderson, SC (US)

(73) Assignee: The Regents of the University of California, Oakland, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/257,889

(22) Filed: Feb. 25, 1999

Related U.S. Application Data

(60) Provisional application No. 60/086,630, filed on May 23, 1998.

(51) Int. Cl.[7] .................................................. C07C 51/42
(52) U.S. Cl. ........................ 562/580; 562/589; 554/184; 554/185
(58) Field of Search .................. 562/580, 589; 554/184, 185

(56) References Cited

U.S. PATENT DOCUMENTS

| | | | | |
|---|---|---|---|---|
| 4,282,323 | * | 8/1981 | Yates | 435/140 |
| 4,323,702 | * | 4/1982 | Kawabata et al. | 562/485 |
| 4,405,717 | * | 9/1983 | Urbas | 435/140 |
| 4,720,579 | * | 1/1988 | Kulprathipanja | 562/580 |
| 5,068,419 | * | 11/1991 | Kulprathipanja et al. | 562/580 |
| 5,412,126 | * | 5/1995 | King et al. | 554/185 |
| 5,510,526 | * | 4/1996 | Baniel et al. | 562/580 |
| 5,965,771 | * | 10/1999 | King et al. | 562/580 |

\* cited by examiner

*Primary Examiner*—Gary Geist
*Assistant Examiner*—Taylor V Oh
(74) *Attorney, Agent, or Firm*—Charles R. Nold; John Mahoney; Paul Martin

(57) ABSTRACT

Carboxylic acids are sorbed from aqueous feedstocks onto a solid adsorbent in the presence of carbon dioxide under pressure. The acids are freed from the sorbent phase by a suitable regeneration method, one of which is treating them with an organic alkylamine solution thus forming an alkylamine-carboxylic acid complex which thermally decomposes to the desired carboxylic acid and the alkylamine.

16 Claims, 7 Drawing Sheets

ACID SORPTION REGENERATION PROCESS USING CARBON DIOXIDE

This application claims benefit of Provisional Application 60/086,630 filed May 23, 1998.

ORIGIN OF THE INVENTION

This invention was made in the performance of work funded by the United States Department of Energy under Contract No. DE-AC03-76SF00098. The United States Government has certain rights to this invention.

TECHNICAL FIELD

The invention is in the field of chemical engineering. In particular, it relates to a process for the recovery of carboxylic acids from aqueous solutions. More particularly, it relates to improvements in sorption extraction processes for recovering carboxylic acids from aqueous streams, utilizing carbon dioxide.

BACKGROUND OF THE INVENTION

Carboxylic acids are important chemicals of commerce. They appear as desired or contaminating constituents of a wide range of aqueous process streams. Historically, they were produced from animal fat or vegetable oil sources or from petroleum sources in substantially nonaqueous systems. More recently, they have been identified among the most attractive products for manufacture from biomass (e.g., corn starch) by fermentation. In these more advanced processes, the carboxylic acid is generated as a dilute solution in an aqueous fermentation broth. Acetic acid is recovered commercially from dilute aqueous solutions by distillation or by extraction with solvents such as isopropyl acetate, other esters, or ethers. Aqueous solutions are created during the manufacture of adipic acid. Citric acid is recovered from fermentation broths commercially by solvent extraction with high-molecular-weight tertiary amines (e.g., tridecylamine) in a diluent composed of a hydrocarbon (e.g., kerosene) and an alcohol (e.g., n-decanol). Citric acid commands a substantial market, which is increasing as detergent manufacturers switch to citric acid as "builder". Lactic acid (raw material for biodegradable plastics), succinic acid, malic acid, fumaric acid, and other carboxylic acids which may be manufactured on a large scale by fermentation of biomass are creating considerable interest in solvent extraction as a means of recovery. Carboxylic acids are also stable oxidation products and frequently appear as by-products or contaminants in aqueous and organic waste streams.

There are numerous current and potential industrial and environmental applications where it is desirable to recover these and other carboxylic acids from aqueous solutions. Examples include the production of citric acid and other acids by fermentation (Lockwood, 1979[1]; Busche, 1985[2]) and removal and recovery of carboxylic acids from aqueous waste streams. (All references noted herein are listed below in a section of the specification entitled "References.") For volatile carboxylic acids, such as acetic, distillation and azeotropic or extractive distillation are alternatives, along with solvent extraction and adsorption (King, 1983[3]; Kuo et al., 1987[4]). For low-volatility carboxylic acids, e.g., dicarboxylic acids and hydroxycarboxylic acids, distillative processes are expensive and often cannot isolate the desired acid.

For acids such as citric and lactic, the classical approach for recovery from a fermentation broth has been to add calcium hydroxide to form the calcium salt of the carboxylic acid, to which an acid such as sulfuric is added to liberate the free carboxylic acid. This approach consumes chemicals (e.g., lime and sulfuric acid) and produces a waste salt stream. Consequently, this method is falling out of favor.

B. Urbas, in U.S. Pat. Nos. 4,405,717[5] and 4,444,881[6], teaches a process for recovering acetic acid, lactic acid, butyric acid and citric acid directly from fermentation broths. This process involves converting the acid to a calcium salt and then adding a tertiary amine carbonate (especially tributylamine carbonate) to give a trialkylammonium salt of the acid and calcium carbonate. The trialkylammonium carboxylate is heated to give the acid and the corresponding trialkylamine. This process has the disadvantage that it generates calcium carbonate, a solid waste that needs to be disposed of or heated to high temperatures in a kiln to convert it back to calcium oxide. Also in these patents, there is a preference for higher molecular weight amines and the use of distillation to remove volatile acids from the less volatile amines.

Solvent extraction is often effective for recovery of these low-volatility carboxylic acids from aqueous solution. Reactive, basic extractants, e.g., tertiary amines or phosphine oxides, can be used to gain greater solvent capacity and selectivity with respect to water and other species. A process developed by Miles, Inc. (Baniel et al., 1981[7]) for recovery of citric acid from fermentation solutions uses a solvent composed of a tertiary amine extractant in a hydrocarbon diluent with an alcohol modifier. This extractant is regenerated by back-extraction of the acid into water at a higher temperature. Back-extraction following a shift in diluent composition, achieved, e.g., by distillation, is another possibility for regeneration, and can be combined with a swing of temperature (Tamada and King, 1990[8,9], and Baniel et al., 1981[7]). The overall degree of concentration relative to the feed that can be achieved by these methods is limited by the extent to which the distribution equilibrium for the carboxylic acid can be changed between forward and back-extraction and also by the feed concentration itself.

Ion exchange and adsorption have also been employed in carboxylic acid recovery schemes. U.S. Pat. No. 4,720,579 to Kulprathipanja[10] discloses the use of styrene-divinylbenzene resins to adsorb citric acid with regeneration by water or by a mixture of acetone and water. Similarly, Great Britain Patent No. 2,064,526A[11] discloses the use of adsorbents containing pyridyl functional groups combined with regeneration by leaching with an organic solvent such as an alcohol or a ketone. U.S. Pat. No. 4,924,027 to Kulprathipanja and Strong[12] discloses adsorption of citric acid by adsorbents containing tertiary amine or pyridyl functionalities (including Bio-Rad AG3-X4A and AG4-X4), with regeneration using an aqueous solution of sodium, potassium or ammonium hydroxide, yielding the respective sodium, potassium or ammonium citrate. Treatment of these citrates with a strong acid would yield the free citric acid form. In each of these solutions the citric acid is adsorbed from an aqueous solution below the $pK_{a1}$ of citric acid.

Many fermentations to produce carboxylic acids operate most effectively at $pH > pK_{a1}$ of the acid, where the acid exists primarily as the carboxylate salt. One example is lactic acid, for which $pK_{a1} = 3.86$[13] and which is produced by fermentation at pH values typically in the range of 5 to 6.[14] For the types of processes under consideration here, the driving force for separation is the concentration of the un-ionized form of the acid.[8,9,15,16,17] Therefore, a compromise is needed between a high pH (above the acid $pK_{a1}$) for the fermentation and a low pH (below the acid $pK_{a1}$) for the separation. A method of recovering the free acid from solution at high pH would be valuable.

Several researchers have used carbon dioxide as an acidulent during solvent extraction of carboxylic acids from the corresponding carboxylate salt solutions. Yates[18] describes a process whereby a carboxylate salt solution is contacted with a water-immiscible polar organic solvent in the presence of carbon dioxide. This patent also describes anion exchange of carboxylate anion with an anion-exchange resin in the bicarbonate form. In this scheme, recovery of the acid is accomplished by regeneration of the resin using a water-containing organic solvent in the presence of carbon dioxide. The carboxylic acid is extracted into the organic solvent, and the resin is reloaded with bicarbonate anion.

Baniel et al.[19] describe a process for recovery of lactic acid from aqueous lactate solutions using reactive extraction with a water-immiscible trialkylamine in the presence of carbon dioxide. Lightfoot et al.[20] similarly describe a process for recovery of lactic acid from aqueous calcium lactate solutions using reactive extraction with a long-chain tertiary or secondary amine in a water-immiscible organic solvent in the presence of carbon dioxide. Hu and Adeyiga[21] presented an analogous study of reactive extraction of formic acid from solutions of sodium formate.

Several advantages exist for using basic solid sorbents, rather than liquid extractants, as complexing agents. Sorption can avoid the problems of emulsion formation and aqueous-phase contamination due to the solubility of the complexing agent and/or diluent(s) that exist with extraction. Although precipitation of low-solubility salts (e.g., $CaCO_3$) could be a concern with fixed beds during sorption, an appropriate choice of cation (e.g., $Na^+$) can avoid this problem for dilute carboxylate solutions.

Historically, as stated above, the conventional technique for recovering non-volatile carboxylic acids from aqueous solution has been precipitation of the calcium carboxylate salt. Both citric and lactic acids are recovered from fermentation broths by this technique.[22] Drawbacks to this approach include substantial energy and chemical costs, loss of product acid because of the solubility of the calcium salt, and production of relatively impure $CaSO_4$.

Recovery technology using reversible chemical complexation with polymeric sorbents having amine functionalities can reduce energy consumption substantially. If a method of regeneration allowing recovery and reuse of all agents is utilized, such processes can also avoid production of waste salts and net consumption of chemical agents. Previous researchers[7,15,16,23–28] have shown that extraction and adsorption by reversible chemical complexation are effective for recovery of carboxylic acids from dilute aqueous solutions. Amine-based extractants and solid sorbents sustain uptake capacity for carboxylic acids from solutions at pH above the $pK_{a1}$ of the acid, where the acid exists mostly as the carboxylate anion.

A shortcoming of using strongly basic complexing agents is that, if a carboxylic acid is removed from an unbuffered solution, the pH will rise sharply if substantial concentrations of strong-base cations (e.g., $Na^+$, $Ca^{2+}$) are present. This pH rise reduces the uptake capacity of the complexing agent and results in low percent recoveries of acid anion. A method is needed to maintain low pH, and thus to sustain the uptake capacity of the complexing agent during the acid recovery step.

One approach for supplying the necessary protons to convert the carboxylate salt into the corresponding acid is to acidify the salt solution directly with a strong acid (e.g., $H_2SO_4$ or $H_3PO_4$). Kulprathipanja et al.[10,12], for example, recovered lactic and citric acids using non-functionalized polystyrene-divinylbenzene sorbents and weak-base anion-exchange resins with acidification by addition of sulfuric acid. Seevaratnam et al.[29] recovered lactic acid from fermentation broths using adsorption and extraction coupled with acidification by addition of hydrochloric acid. In both of these cases, the pH of the fermentation broth must be adjusted with base if it is to be returned to the fermentor. Thus, one major disadvantage of recovering carboxylic acids by extraction or adsorption with strong-acid addition is that acid and base are consumed, and salts build up in the broth and must be removed. Additionally, competitive sorption can occur between the strong-acid anions and the carboxylate anions.[30]

Cation exchange to replace the strong-base cations in solution with protons avoids the problem of introducing strong-acid anions (e.g., $SO_4^{2-}$, $PO_4^{3-}$) into solution. Cation exchange does not offer any solution to the problem of waste salt formation, however. When the cation-exchange resin is depleted of protons, it must be regenerated with a strong acid—most often $H_2SO_4$—resulting in the production of a sulfate salt waste stream.

Addition of a suitable buffer to the solution has the potential to prevent the pH-swing associated with acid recovery. This buffer would need to be added at a sufficient concentration to provide a large buffering capacity, without incurring detrimental effects to the microorganisms if it is applied directly to a fermentation. It should also have a $pK_a$ similar to the pH that one is trying to maintain and should not compete effectively with the carboxylic acid for the basic sites on the sorbent.

As can be seen from the foregoing, various methods used heretofore to recover carboxylic acids have presented limitations and thus offer opportunities for improvement.

One such improved process is described and claimed in U.S. Pat. No. 5,412,126, King et al.[31], and incorporated by reference herein. In this process, carboxylic acid is sorbed from an aqueous feedstock into an organic liquid phase or onto a solid adsorbent. The acid is freed from the sorbent phase by treating it with aqueous, low-molecular-weight alkylamine thus forming an alkylammonium carboxylate which is dewatered and decomposed to the desired carboxylic acid and the alkylamine.

Another variation, as described in Ind. Eng. Chem. Res. 1998, 37, 2996–3005, Husson and King[32], also U.S. patent application Ser. No. 08/943,514, filed Oct. 3, 1997, both of which are incorporated by reference herein, is to sorb the carboxylic acid onto a solid basic adsorbent, then regenerate it by treating the sorbed mass with an organic solution of an alkylamine. The alkylamine-carboxylic acid complex thus formed is thermally decomposed to provide the desired acid and alkylamine.

It has now been found, however, that no matter which of the above indicated processes is used, it can be further improved upon and made more efficient by using carbon dioxide under pressure during the first step of the process in which the carboxylic acid containing feedstream is contacted with the acid-sorbing phase.

It is accordingly a general object of the invention to provide an efficient process for the recovery of carboxylic acids from aqueous solutions which neither consumes large amounts of chemicals nor generates waste chemical streams.

It is a further object to provide a process for the recovery of free carboxylic acid from an aqueous solution at a high pH.

It is yet another object of the invention to provide a process for the recovery of free carboxylic acid from an aqueous solution where the pH of the solution is greater than the $pK_a$ of the acid.

It is a still further object of the invention to provide an efficient process for the recovery of carboxylic acid where the process is carried out in the presence of carbon dioxide.

LITERATURE REFERENCES

The following references are known to one or more of the present inventors and relate to the general subject matter of the present invention:

1. Lockwood, L. B. Production of Organic Acids by Fermentation. In *Microbial Technology;* Peppler, H. J.; Perlman, D. Eds.; Academic Press: New York, 1979; 356–387.

2. Busche, R. M. The Business of Biomass. *Biotechnology. Prog.* 1985, 1, 165–180.

3. King, C. J. Acetic Acid Extraction. In *Handbook of Solvent Extraction*; Lo, T. C.; Baird, M. H. I.; Hanson, C., Eds.; Wiley-Interscience: New York, 1983.

4. Kuo, Y.; Munson, C. L.; Rixey, W. G.; Garcia, A. A.; Frierman, M.; King, C. J. Use of Absorbents for Recovery of Acetic Acid from Aqueous Solutions. I. Factors Governing Capacity. *Separ. Purif. Methods* 1987, 16, 31–64.

5. Urbas, B. Recovery of Acetic Acid from a Fermentation Broth. U.S. Pat. No. 4,405,717, 1983.

6. Urbas, B. Recovery of Organic Acids from a Fermentation Broth. U.S. Pat. No. 4,444,881, 1984.

7. Baniel, A. M.; Blumberg, R.; Hajdu, K. Recovery of Acids from Aqueous Solutions. U.S. Pat. No. 4,275,234, 1981.

8. Tamada, J. A.; King, C. J. Extraction of Carboxylic Acids with Amine Extractants. II. Chemical Interactions and Interpretation of Data. *Ind. Eng. Chem. Res.* 1990, 29, 1327–1333.

9. Tamada, J. A.; King, C. J. Extraction of Carboxylic Acids with Amine Extractants. III. Effect of Temperature, Water Co-Extraction and Process Considerations. *Ind. Eng. Chem. Res.* 1990, 29, 1333–1338.

10. Kulprathipanja, S. Separation of Citric Acid from Fermentation Broth with a Neutral Polymeric Adsorbent. U.S. Pat. No. 4,720,579, 1988.

11. Kawabata, N.; Yasuda, S.; Yamazaki, T. Process for Recovering a Carboxylic Acid. Great Britain Patent No. 2,064,526, 1982.

12. Kulprathipanja, S.; Strong S. A. Separation of Salts of Citric Acid from Fermentation Broth with a Weakly Basic Anionic Exchange Resin Adsorbent. U.S. Pat. No. 4,924,027, 1990.

13. Holten, C. H. *Lactic Acid: Properties and Chemistry of Lactic Acid and Derivatives*; Verlag Chemie: Copenhagen, 1971.

14. Vickroy, T. B. Lactic Acid. In *Comprehensive Biotechnology;* Blanch, H. W.; Drew, S.; Wang, D. I. C., Eds.; Pergamon: New York, 1985; Vol. 3, Chapter 38.

15. Kertes, A. S.; King, C. J. Extraction Chemistry of Fermentation Product Carboxylic Acids. *Biotechnol. Bioeng.* 1986, 28, 269–282.

16. Tamada, J. A.; Kertes, A. S.; King, C. J. Extraction of Carboxylic Acids with Amine Extractants. I. Equilibria and Law-of-Mass-Action Modeling. *Ind. Eng. Chem. Res.* 1990, 29, 1319–1326.

17. Yang, S. T.; White, S. A.; Hsu, S. T. Extraction of Carboxylic Acids with Tertiary and Quaternary Amines: Effect of pH. *Ind. Eng. Chem. Res.* 1991, 30, 1335–1342.

18. Yates, R. A. Removal and Concentration of Lower Molecular Weight Organic Acids from Dilute Solutions. U.S. Pat. No. 4,282,323, 1981.

19. Baniel, A. M.; Eyal, A. M.; Mizrahi, J.; Hazan, B.; Fisher, R.; Kolstad, J. J.; Stewart, B. F. Lactic Acid Production, Separation and/or Recovery Process. U.S. Pat. No. 5,510,526, 1996.

20. Lightfoot, E. N.; de Pablo, J. J.; Cockrem, C. M.; Miller, R. W. Extraction of Lactic Acid from a Calcium Lactate Solution Using Amine-Containing Solvents and Carbon Dioxide Gas. *Ind. Eng. Chem. Res.* 1996, 35, 1156–1162.

21. Hu, L.; Adeyiga, A. A. Extraction of Formic Acid from Sodium Formate. *Ind. Eng. Chem. Res.* 1997, 36, 2375–2379.

22. Datta, R. Hydroxycarboxylic Acids. In *Kirk-Othmer Encyclopedia of Chemical Technology;* Kroschwitz, I.; Howe-Grant, M., Eds.; John Wiley & Sons: New York, 1995; Vol. 13, 1042–1062.

23. Yabannavar, V. M.; Wang, D. I. C. Bioreactor System with Solvent Extraction for Organic Acid Production. *Ann. NY Acad. Sci.* 1987, 506, 523–535.

24. Yabannavar, V. M.; Wang, D. I. C. Extractive Fermentation for Lactic Acid Production. *Biotechnol. Bioeng.* 1991, 37, 1095–1100.

25. Garcia, A. A.; King, C. J. The Use of Basic Polymeric Sorbents for the Recovery of Acetic Acid from Dilute Aqueous Solution. *Ind. Eng. Chem. Res.* 1989, 28, 204–212.

26. Tung, L. A.; King, C. J. Sorption and Extraction of Lactic and Succinic Acids at $pH>pK_{a1}$. 1. Factors Governing Equilibria. *Ind. Eng. Chem. Res.* 1994, 33, 3217–3223.

27. Tung, L. A.; King, C. J. Sorption of Carboxylic Acid from Carboxylic Salt Solutions at pHs Close to or above the $pK_a$ of the Acid, with Regeneration with an Aqueous Solution of Ammonia or Low-Molecular-Weight Alkylamine. U.S. Pat. No. 5,132,456, 1992.

28. Kirsch, T.; Maurer, G. Distribution of Binary Mixtures of Citric, Acetic and Oxalic Acids between Water and Organic Solutions of Tri-n-octylamine. Part I. Organic Solvent Toluene. *Fluid Phase Equilibria* 1997, 131, 213–231.

29. Seevaratnam, S.; Hoist, O.; Hjörleifsdottir, S.; Mattiasson, B. Extractive Bioconversion for Lactic Acid Production Using Solid Sorbent and Organic Solvent. *Bioprocess Eng.* 1991,6,35–41.

30. Tung, L. A. Recovery of Carboxylic Acids at $pH>pK_{a1}$. Ph.D. Dissertation, University of California, Berkeley, Calif., 1993.

31. Poole, L. J.; King, C. J. Carboxylic Acid Sorption Regeneration Process. U.S. Pat. No. 5,412,126, 1995.

32. Husson, S. M.; King, C. J. Regeneration of Lactic and Succinic Acid-Laden Basic Sorbents by Leaching with a Volatile Base in an Organic Solvent. *Ind. Eng. Chem. Res.* 1998, 37, 2996–3005.

33. Atkins, P. W. *Physical Chemistry;* W. H. Freeman: New York, 1990.

34. Husson, S. M. Regeneration of Basic Adsorbents in the Recovery of Carboxylic Acids from Dilute Aqueous Solution and Multiple-acid Equilibria in the Recovery of Carboxylic Acids from Dilute Aqueous Solution. Ph.D. Dissertation, University of California, Berkeley, Calif., 1998.

35. Gustafson, R. L.; Fillius, H. F.; Kunin, R. Basicities of Weak Base Ion Exchange Resins. *Ind. Eng. Chem. Fundam.* 1970, 9, 221–229.

36. Garcia, A. A. The Modification and Use of Adsorbents for the Recovery of Acetic Acid from Dilute Aqueous Solutions. Ph.D. Dissertation, University of California, Berkeley, Calif., 1988.

37. Clifford, D; Weber, W. J., Jr. The Determinants of Divalent/Monovalent Selectivity in Anion Exchangers. *React. Polym.* 1983, 1, 77–89.

BRIEF DESCRIPTION OF THE DRAWINGS

In this description of the invention, reference will be made to the accompanying figures and drawings, in which.

SUMMARY OF THE INVENTION

Figure 1:
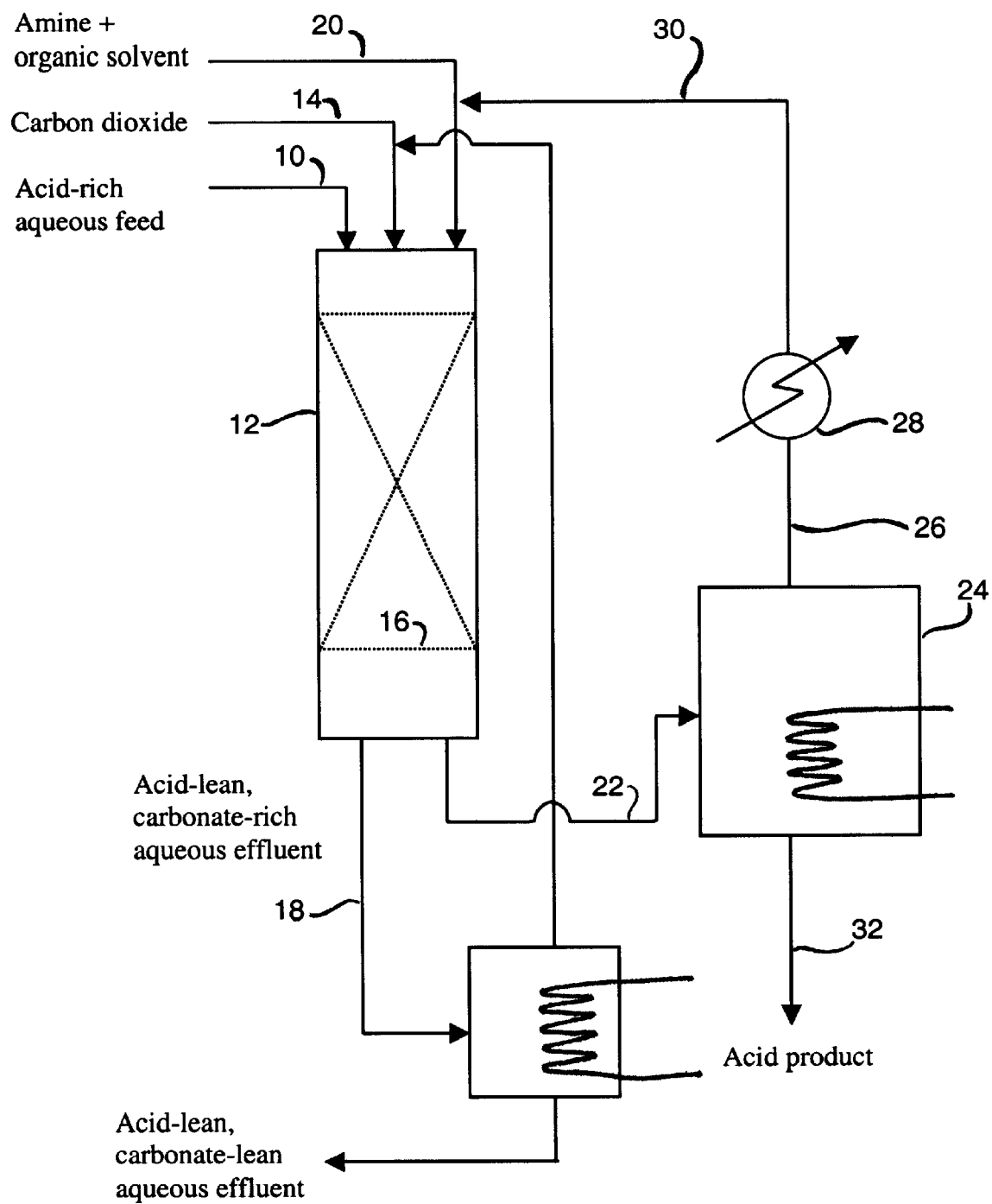
FIG. 1. Schematic flow diagram illustrating one embodiment of the process of the invention.

The present invention is a process for recovering free carboxylic acid from an aqueous feedstream in which the carboxylic acid may be a salt and/or a free acid. It has been found that carbon dioxide can be used in conjunction with basic complexing agents to avoid the problem of pH rise and, therefore, to sustain uptake capacity at $pH > pK_{a1}$. The addition of carbon dioxide ($pK_{a1}=6.37$ at 25° C.[33]) to an aqueous carboxylate salt solution results in formation of the corresponding carboxylic acid:

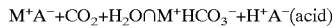

where $M^+$ is a cation (e.g., $Ca^{2+}$, $Na^+$). The free acid can then be recovered by reversible reaction with a basic solid sorbent. The sorbent can be regenerated by any one of a number of techniques known in the art, some of which have been mentioned above. By use of an appropriate method of regeneration, allowing recovery and reuse of all agents, this sorption-regeneration scheme avoids chemical consumption and waste salt generation; all materials are recoverable and recyclable, including carbon dioxide. The high volatility of carbon dioxide is useful for this purpose.

In the adsorption process described and claimed herein, the carboxylic acid is first removed from an aqueous feed stream by a solid-phase adsorption, or sorption, technique with a basic solid sorbent in the presence of carbon dioxide. Here, sorption connotes uptake by a solid that may be either or both surface (adsorption) or bulk (absorption) phenomena. The sorbed carboxylic acid is then recovered by a suitable regeneration process. In one embodiment of the process, regeneration is accomplished by contacting the sorbent phase with an organic solution of a volatile base that is sufficiently basic in comparison with the sorbent. This regeneration technique is described elsewhere in reference 32, which reference is incorporated herein in its entirety.

As stated in the publication, this embodiment of the process, in its entirety, comprises removal of the selected carboxylic acid from an aqueous feedstream by solid-phase sorption with a basic sorbent, then recovery of the sorbed carboxylic acid by contacting the sorbed phase with an organic solution of a volatile base that is sufficiently basic in comparison with the sorbent. This "back extracts" or solubilizes the carboxylic acid into the organic phase as an acid-base complex. The organic solution containing the acid-base complex is heated to decompose the complex fully to yield the carboxylic acid product. The volatile base is then recovered and recycled.

In this embodiment, when viewed as an overall process, the carboxylic acids are first removed from the aqueous feed stream by a sorption technique, such as a solid-phase adsorption. This step is carried out in the presence of carbon dioxide under pressure. The sorbed carboxylic acid is then recovered by contacting the sorbent phase with an organic solution of a low-molecular-weight alkylamine. This "back-extracts" the carboxylic acid into the organic extraction phase as an alkylamine-carboxylic acid complex. When this organic solution is heated, the alkylamine-carboxylic acid complex decomposes to give rise to the carboxylic acid which can then be recovered. The alkylamine is also regenerated and can be recycled. Thus, a process is achieved which consumes no significant amount of chemicals and generates no significant amounts of waste by-product.

In one aspect, therefore, the present invention provides a process for isolating carboxylic acids from carboxylic acid-containing aqueous streams in which the adsorption step is carried out in the presence of carbon dioxide. Thereafter, the acid is recovered by any one of a number of techniques known by those skilled in the art, one of which is back-extraction with an organic solution of a volatile alkylamine.

In another aspect, the present invention provides an overall process for recovering carboxylic acids from a carboxylic acid-containing aqueous feedstream. This process involves the following steps:

(a) The carboxylic acid-containing feedstream is first contacted with an acid-sorbing phase under conditions whereby the carboxylic acid is sorbed from the feedstream to the acid-sorbing phase. The acid-sorbing phase can be a solid or gel, ion-exchanger or other solid acid sorbing material. This step is carried out in the presence of carbon dioxide under pressure. This first step of the process forms an acid-depleted aqueous feedstream which can be discarded or further processed or recycled, as desired. It also provides an acid-enriched acid-sorbing phase.

(b) The acid-enriched acid-sorbing phase is then isolated.

(c) The isolated acid-enriched acid-sorbing phase is then regenerated. In one method, it is contacted with an organic solution of low-molecular-weight alkylamine. The alkylamine solubilizes the carboxylic acid from the sorbing phase into the organic solution as an alkylamine-carboxylic acid complex. This has the effect of regenerating the acid-sorbing phase so that it may be reused.

(d) The organic solution containing the low-molecular-weight alkylamine-carboxylic acid complex is then separated from the regenerated acid-sorbing phase.

(e) In the fifth step of this process, the organic solution of alkylamine-carboxylic acid complex is treated, under conditions such as by mild heating, to decompose the alkylamine-carboxylic acid complex into the alkylamine and the carboxylic acid, either as crystals or as a highly saturated solution, depending upon the tendency of the carboxylic acid to crystallize. The carboxylic acid can be simply recovered from this product. The alkylamine can also be taken off to drive the reaction in the direction of the desired decomposition and recovered, for example, as an overhead in distillation and recycled.

DESCRIPTION OF PREFERRED EMBODIMENTS

The Process

The process of this invention can be employed in any of the known methods for contacting solid sorbents with fluid phases. Such a process is shown representatively in FIG. 1. In FIG. 1, an acid-rich aqueous feed is charged through line 10, to a fixed bed of solid or gel sorbent 12. Carbon dioxide is injected under pressure through line 14. Unit 12 contains a bed of solid sorbent, for example, ion exchange material 16. This solid or gel sorbent may be a relatively basic material such as an amine-containing resin or the like so as to adsorb selectively the carboxylic acid groups out of the acid-rich aqueous feed. The sorbent thus gives rise to an acid-lean aqueous outflow which is taken out of contactor 12 via line 18. The outflow in line 18 can be suitably monitored until a breakthrough in carboxylic acid level is noted in the outflow, indicating that the solid sorbent 16 has removed its capacity of carboxylic acid. At this point, feedline 10 is closed via means not shown and aqueous outflow line 18 is also closed. An organic solution of low-molecular-weight alkylamine is then fed to contactor 12 via line 20. The low-molecular-weight alkylamine and the solid sorbing phase are matched so that the low-molecular-weight amine is a stronger base than the sorbent employed. This causes the low-molecular-weight alkylamine to react with the sorbed carboxylic acid and form an alkylamine-carboxylic acid complex, which is soluble in the organic solvent and thus carried out of contactor 12 via line 22. This stream is then passed to decomposing zone 24. The stream is heated so as to give rise to a vapor stream made up of the alkylamine and other constituents. Zone 24 produces a bottom product containing the recovered carboxylic acid which is removed via line 32.

In the process shown in FIG. 1, the amount of lower alkylamine should be so that if complete recovery of carboxylic acid is desired, at least about one equivalent of low-molecular-weight alkylamine should be used for each equivalent of acid being recovered. Depending upon the functionality of the carboxylic acid and the equilibrium of the reaction between the alkylamine and the carboxylic acid, it may be necessary to use more than one equivalent of amine per equivalent of carboxylic acid. If a lower degree of recovery can be tolerated or is desired, lower amounts of alkylamine may also be used.

It is generally preferred to carry out the steps of this process (other than the first step which is carried out in the presence of carbon dioxide), especially the decomposition, in an oxygen-free or reduced-oxygen environment such as an inert gas blanket to minimize decomposition of the amine itself.

The acid recovered via line 30 is typically present as a slurry of solid in organic liquid or as a saturated/supersaturated solution of acid. This stream can be further processed to enable further treatment of the acid-containing material, to decolorize and deodor it, further remove amine from it and otherwise purify it. These steps are optional.

This process can be practiced in a batch mode, as well, if desired, and in various other embodiments for contacting solid sorbents and fluid phases, e. g., continually changing feed and withdrawal positions along a fixed bed or a series of fixed beds.

The Acids Recovered

The acids liberated and recovered in the regeneration process of the invention are carboxylic acids. These acids include aliphatic carboxylic acids of 2–16 carbons and aromatic carboxylic acids of 7–20 carbons. The aliphatic carboxylic acids include 2–16 carbon monoacids such as acetic acid, propionic acid, butyric acid, pentanoic acid, hexanoic acid, octanoic acid, dodecanoic acid and the like. The process is especially effective with carboxylic acids containing multiple carboxylic groups, such as the di-, tri-, and higher carboxyl materials, including the commonly known even-carbon-numbered diacids of 2–12 carbons (that is, the better known dicarboxylic acids of 2, 4, 6, 8, 10 or 12 carbon atoms, such as oxalic acid, succinic acid, sebacic acid, adipic acid and fumaric acid). Of course, the process also works with the odd-numbered acids, as well. Lactic acid, malic, acid and citric acid are representative hydroxy-containing acids which can be recovered by this process.

The aromatic acids include aromatic monoacids of 7–13 carbons such as benzoic acid, cinnamic acid, phenylacetic acid, naphthoic acid, and the like, and diacids of 8–12 carbons such as phthalic acid. In addition to the simple oxyhydrocarbon acids, the process can be used, under appropriately chosen conditions, to recover those more complex materials such as amino acids, and the like, which are of value and which often occur in aqueous solutions and need to be recovered therefrom.

Functional groups such as halogens or nitro groups may be present in the carboxylic acids recovered by the process of this invention.

When these acids are initially present in and recovered from water-based feedstocks in an overall sorption-regeneration process, the feedstocks will contain from about ten parts per million to saturation (for example, up to about 40% by weight) and especially from 0.1% to 25% by weight of recoverable carboxylic acids. The feedstocks can contain a mixture of these acids, in which case the present process can either recover all of the acids or, if differences in forward sorption or back-extractability with the alkylamine permit, can fractionate the acid mixture. The present invention finds application with prepared feedstocks such as fermentation broths and the like; it also finds application with contaminated aqueous streams. Accordingly, the feedstocks can contain other materials such as salts and organics (sugars, starches, alcohols, aldehydes and the like). Typically, however, with well chosen sorbents and regenerants, these other materials do not substantially follow the carboxylic acids as they are sorbed and back-extracted. Thus, they do not significantly interfere with the process of this invention.

As noted, these acid materials removed and recovered by the process range in size from about 2 carbons (acetic acid) to about 16 carbons and can include monocarboxylic acids, di- and polycarboxylic acids, hydroxycarboxylic acids, and the like. The acid can be aliphatic or aromatic. This wide range of materials spans a range of physical forms: A few of these acids, for example, the 2 to 4 carbon monocarboxylic acids, are relatively volatile liquids.

| $C_2$ - Acetic Acid | 118° C. b.p. |
|---|---|
| $C_3$ - Propionic Acid | 141° C. b.p. |
| $C_4$ - Butyric Acid | 165° C. b.p. |

Lactic acid is hard to crystallize and usually exists as a concentrated viscous solution. Many of the rest of these acids, especially the dicarboxylic acids, exist as solids with low solubilities at room temperature. The physical form of the free acids can play a part in the selection of the low-molecular-weight alkylamine employed in the regeneration.

As noted previously, in the decomposition steps of the regeneration process, a forward driving force is needed to assure substantial conversion of the alkylamine-carboxylic acid complex. This driving force typically is provided by separating the free amine from the free acid and removing one or both products from the reaction zone. Preferential vaporization of one product from the other is a very convenient and preferred way to carry out this separation.

The Low-molecular-weight Alkylamine

A key element of the embodiment of the process of the present invention using an organic alkylamine as regenerant is the use of that as the back-extractant (desorbant) material. This alkylamine material is also sometimes referred to herein as a low-molecular-weight amine or the like.

The lower alkylamine can be a mono-, di- or trialkylamine.

Of these materials, the trialkylamines offer an advantage of not being capable of forming amides with the recovered acids. The mono- and dialkyl materials can enter into this irreversible side reaction if prolonged contact with the acid at elevated temperatures occurs.

Another factor to be taken into account in selecting an amine is its volatility relative to the aqueous back-extraction solvent and the free acid. If volatilization of the amine is to be used as the mechanism to separate the amine from the acid, a difference between them in volatility over the organic solvent is necessary.

Still another factor to be taken into account in selection of an amine is the susceptibility of the amine to thermal decomposition and/or oxidation.

Of the trialkylamines, preference is given to trimethylamine for a number of reasons. First, it is the most common and least expensive of these materials. Also, it has a high solubility in organic solvents and thus allows a concentrated back-extract to be formed. Third, it is the most volatile of the trialkylamines (2.9° C. b.p.) and thus, during decomposition of the trimethylamine-carboxylic acid complexes, can be removed overhead by distillation with the least amount of heating of the solution containing the trimethylamine-carboxylic acid complexes and resulting acid. Other trialkylamines containing up to about 6 or even 8 total carbon atoms—for example, dimethylethylamine, methyldiethylamine, triethylamine, dimethyl-n-propylamine, dimethyl-i-propylamine, methyldi-n-propylamine, dimethylbutylamine and the like—may be used. Monoalkylamines of up to about 6 carbons such as methylamine, ethylamine, propylamine, butylamine, pentylamine and hexylamine and dialkylamines of up to about 8 total carbons such as dimethylamine, diethylamine, dibutylamine and the like can also be used as long as their potential for side reactions is kept in mind. Mixtures of amines can be used.

In the embodiment under consideration, these alkylamines are employed as an organic solution. This solution is generally made as concentrated in amine as possible. It can, however, range in concentration from about 1% to saturation, which is about 25%–50% by weight in the case of the more soluble of these amines, such as trimethylamine. The organic solution of alkylamine can contain other materials added to improve or facilitate processing. These can include modifiers, antifoam agents, corrosion inhibitors, and the like, as will be known to those of skill in the art. The amine concentration can be increased by dissolving under pressure of up to about 5 atmospheres as well.

The Organic Solvent

The organic-phase liquid or solvent in which the alkylamine is dissolved can be a single material or it can be a mixture of materials. Ketones having 4 to 8 carbons, for example methyl isobutyl ketone, methyl n-butyl ketone, methyl pentyl ketone, diethyl ketone and the like, can be used as extracting solvents. Cyclic ketones have given very good results. These contain from 5 to about 10 carbons with 5 or 6 carbons making up a 5- or 6-membered aliphatic ring and the remainder being alkyl substituents off the ring. Cyclopentanone, cyclohexanone, methyl cyclohexanone, dimethyl cyclohexanone, and diethyl cyclohexanone are examples of suitable organic-phase liquids for use herein. Six to 10 carbon alcohols such as n-hexanol, cyclohexanol, heptanol, n-octanol, 2-ethyl hexanol, nonanol, and the like can be used. Four- to 8-carbon ethers such as diethyl ether, methyl butyl ether, methyl pentyl ether, and ethyl butyl ether can also be used. Five to 8 carbon esters such as butyl acetate, pentyl acetate, and the like can be used as well.

The solvent which is selected should meet the following criteria. The solvent should (1) not react irreversibly with the acid, the organic base, or the sorbent, (2) be easily removed from the sorbent under conditions that do not degrade the sorbent, (3) be sufficiently different in volatility to be easily removed from the acid, and (4) have a high solubility for the organic base.

Solid Sorbent Materials

The preferred solid-phase basic acid sorbers for use in the process of this invention include resins such as pyridyl, pyridinium, amine and ammonium group-containing resins. These materials include resins with these groups as part of their backbone structure as well as materials which have these groups appended from their backbones. These resin materials are available commercially as basic solid-phase resins. Representative resins are listed in Table 1.

TABLE 1

Basic Solid Adsorbents

| Commercial Designation | Source | Type of Adsorbent |
|---|---|---|
| AMBERLITE | | |
| IRA-35 | Rohm & Haas Corp. | Acrylic-divinylbenzene with tertiary-Amine groups |
| XAD-12 | Rohm & Haas Corp. | Poly (N oxide) |
| XE-309 | Rohm & Haas Corp. | Poly (4-Vinylpyridine) |

TABLE 1-continued

Basic Solid Adsorbents

| Commercial Designation | Source | Type of Adsorbent |
|---|---|---|
| XE-378 DOWEX | Rohm & Haas Corp. | Poly (2-Vinylpyridine) |
| WGR | Dow Chemical Company | Epoxy Polymer with Tertiary Amine Groups |
| MWA-1 | Dow Chemical Company | Styrene-Divinylbenzene Copolymer with Tertiary-Amine Groups |
| A-340 | Diamond Shamrock, Inc. | (Duolite) Polyethylene-Diamine, Cross-Linked with Epichlorohydrin (a gel-type resin) |
| AG3-X4 | Bio-Rad | Epoxy-amine Polymer with Primarily Tertiary Amine Groups and 10% Quaternary Groups |
| REILLEX 425 | Reilly Tar & Chemical Co. | Poly(4-Vinylpyridine) |

Experimental Materials and Methods

Materials. Chemical Reagents. Reagents and sources are tabulated in the Ph.D. dissertation of Scott Husson, 1998, on file in the library at the University of California, Berkeley, which dissertation is incorporated herein by reference in its entirety.[34] All aqueous solutions were prepared from distilled water that had been passed through a Milli-Q water purification system (Millipore Corp.). Lactic acid (85+wt. %) was diluted with water to approximately 15 wt. % and boiled under constant reflux for at least 12 hours to hydrolyze any lactic acid polymers. Complete hydrolysis of the esters was confirmed by high-performance liquid chromatography (HPLC).

Sorbents. The polymeric sorbents utilized were Dowex MWA-1 (Dow Chemical Co.) and Amberlite IRA-35 (Rohm and Haas Co.). Both sorbents are commercially available and are macroreticular. Tung and King[26] provide a detailed discussion of the chemical structures, measured capacities and basicities of these and several other polymeric sorbents. This published article is incorporated herein by reference. Prior to use, the sorbents were washed repeatedly with aqueous hydrochloric acid, aqueous sodium hydroxide, water and methanol; further purified by Soxhlet extraction with methanol for at least 24 hours; and dried to constant weight in a vacuum oven at 60° C. and 15–25 kPa.

Aqueous Sodium Lactate Solutions. Aqueous solutions of sodium lactate were prepared from aqueous solutions of lactic acid and sodium hydroxide. Initial sodium lactate concentrations ranged from 0.05 M to 0.40 M, with corresponding initial pH values of 8.28 to 8.71.

Methods. Sorbent Loading The equilibrium cell used in all of the $CO_2$-sustained acid sorption experiments consisted of a 125-mL glass vial with a crimp-cap seal lined with a 3-mm thick silicone septum. The vial was placed in a constant-temperature bath maintained at 25° C. by a temperature controller.

Known weights of Dowex MWA-1 or Amberlite IRA-35 sorbent (typically 5 g) and sodium lactate solution (typically 50 g) were contacted in the cell. The solution was stirred continuously with a magnetic stir bar. To purge the system of air, $CO_2$ was introduced to the vial through a syringe needle connected to a pressurized $CO_2$ gas cylinder. Air and $CO_2$ exited the vial through a second syringe needle connected to a bubble flow meter which served to measure the flow of $CO_2$ into the vial. To ensure that essentially all of the air was removed from the vapor space, experiments were conducted to measure the equilibrium uptake of lactate anion from a 0.05 M sodium lactate solution onto Dowex MWA-1 as a function of $CO_2$ purge volume.

When the system had been purged of air, the syringe needle connected to the bubble flow meter was removed from the vial, and the system was pressurized with $CO_2$ to the desired working pressure (10–320 kPa gauge). The syringe needle connected to the $CO_2$ cylinder was left in place to ensure that the pressure did not change in the event of any system leaks. After 24 hours, the concentration of lactate in the solution was measured, and the amount of lactate removed by adsorption of lactic acid onto the sorbent was calculated. Additional measurements showed that equilibrium was reached within the experimental error in the batch equilibration experiments within 3 hours.[34] Aqueous-phase acid concentrations were determined by HPLC using a Bio-Rad Aminex HPX-87H strong cation-exchange column or a Bio-Rad Fast-acid-analysis column maintained at 60° C., a 0.01 N $H_2SO_4$ mobile phase, and an ultraviolet detector operating at 210 nm.

Measuring Lactate and Bicarbonate Anion-Exchange Isotherms. Dowex MWA-1 contains approximately 10% quaternary ammonium sites among the tertiary amine sites.[35] Lactate and bicarbonate anion-exchange isotherms for the quaternary-ammonium sites of Dowex MWA-1 were measured by contacting known weights of dry sorbent (typically 0.5 g) with known weights of sodium lactate or bicarbonate solution (typically 5 g) in 20-mL scintillation vials sealed with Teflon®-lined caps. The vials were placed in a constant-temperature, reciprocating shaker bath at 25° C. and 120 RPM for at least 24 hours. Aqueous-phase lactate concentrations were determined by HPLC, as previously described. Aqueous-phase bicarbonate concentrations were determined by titration to potentiometric endpoint.

Fixed-bed Adsorption of Lactic Acid Aided by Carbon Dioxide. A known dry mass of Dowex MWA-1 sorbent was pre-wet with methanol and fed as a slurry to a 1-cm I.D.×30-cm length glass column wherein it settled into a fixed bed. Pure water was fed to the column via PTFE tubing connected to an adjustable plunger at the top of the column so as to displace the methanol from the sorbent. All aqueous sodium lactate solutions were delivered to the top of the column with a peristaltic pump at a controlled volumetric flow rate. Effluent samples from the column were collected over specified time intervals in glass scintillation vials using a fraction collector. Lactate anion concentrations in the effluent samples were measured by HPLC, as previously described.

Three experiments were performed with Dowex MWA-1 sorbent to examine the effect of $CO_2$ pressure on lactate adsorption. In each experiment, the feed solution was a 0.05 M aqueous sodium lactate solution. The first experiment measured the breakthrough curve of lactate anion in the absence of $CO_2$. In subsequent experiments, the feed solutions were equilibrated with $CO_2$ at pressures of 100 and 300 kPa gauge in a 125-mL glass vial sealed with a silicone septum. The column pressure was also maintained at elevated pressure by a valve at the column outlet to prevent $CO_2$ coming out of solution within the column.

Amberlite IRA-35 sorbent was also used, so as to examine the effect of sorbent basicity on lactate breakthrough. The experimental procedure was identical to that for Dowex MWA-1, except that Amberlite IRA-35 was used in the water-wet form and was fed to the column as a slurry in water. The dry mass of the sorbent was determined gravimetrically.

Additional experiments were performed with Amberlite IRA-35 to examine the effect of volumetric flow rate on lactate anion breakthrough. Aqueous sodium lactate solutions were delivered to the top of the column at controlled volumetric flow rates of 4.7, 12.1 and 18.9 bed volumes per hour. In each experiment, the feed solution was a 0.05 M aqueous sodium lactate solution equilibrated with $CO_2$ at a pressure of 300 kPa gauge. For the experiment at 4.7 bed volumes per hour, the rate of volume expansion of the bed was measured by recording the bed height versus time. Bed height was measured with a cathetometer.

Additional details on the experiments, including schematic representations of the apparatuses, are available elsewhere, and incorporated herein by reference.[34]

Results

Effect of Carbon Dioxide Purge Volume on Equilibrium Uptake. Experimental measurements[34] showed that for purge volume-to-vapor ratios greater than 3 essentially all of the air initially present in the vapor space was removed. The lactic acid uptake became constant at this and greater purge volumes.

EXAMPLES 1 and 2

Figure 2:
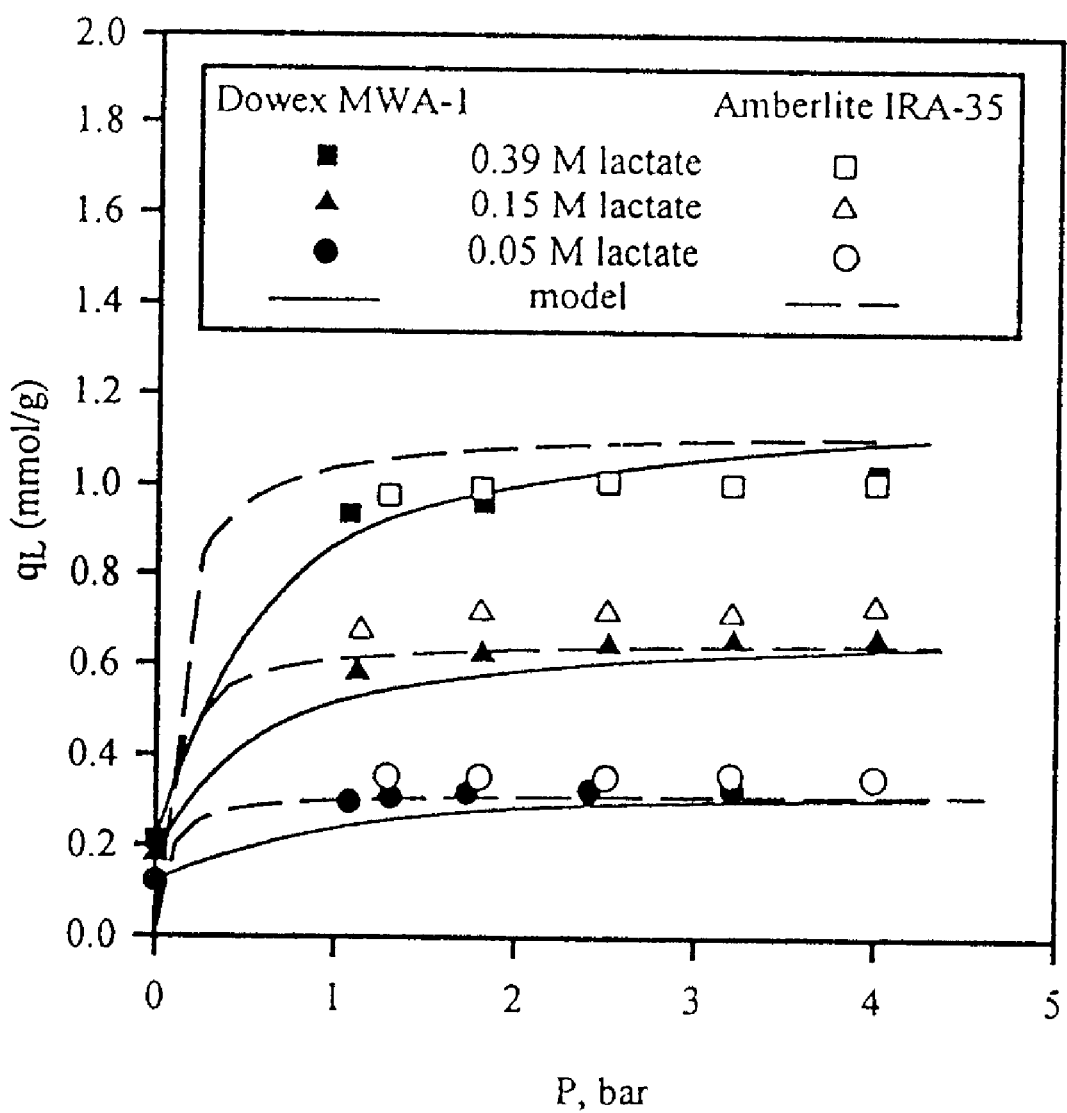
FIG. 2. Equilibrium uptake isotherms for $CO_2$-sustained adsorption of lactic acid onto Dowex MWA-1 and Amberlite IRA-35 at 25° C. from 0.05 M, 0.15 M and 0.39 M sodium lactate solutions. The symbols at P=0 for Dowex MWA-1 represent uptake in the absence of $CO_2$. The curves represent the predictions of a model.

Adsorption of Lactic Acid in the Presence of Carbon Dioxide. FIG. 2 shows the equilibrium uptake isotherms for $CO_2$-sustained adsorption of lactic acid onto Dowex MWA-1 and Amberlite IRA-35, respectively, at 25° C. from 0.05 M, 0.15 M and 0.39 M solutions of sodium lactate. Experimental data are represented by symbols. The curves represent a mathematical model to describe adsorption equilibria for these systems, employing empirically estimated values of K=200.3 g soln/g acid and K=2643.9 g soln/g acid for adsorption of hydrated carbon dioxide at 25° C. onto Dowex MWA-1 and Amberlite IRA-35, respectively. The symbols at P=0 for Dowex MWA-1 represent the uptake of lactate anion by ion exchange from 0.05 M, 0.15 M and 0.39 M sodium lactate solutions in the absence of $CO_2$.

For Dowex MWA-1, the highest experimental uptake values for adsorption from solutions of 0.05 M, 0.15 M and 0.39 M sodium lactate correspond to 65.5%, 43.9% and 26.3% recovery of lactate anion from the initial solution, respectively. These percent recoveries are substantially higher than the corresponding percent recoveries of 23.0%, 11.5% and 5.2% in the absence of $CO_2$. Despite being more strongly basic than Dowex MWA-1, Amberlite IRA-35 shows only slightly higher uptake values for adsorption of lactate anion. The highest experimental uptake values for adsorption from solutions of 0.05 M, 0.15 M and 0.39 M sodium lactate correspond to 72.0 %, 48.7 % and 25.9 % recoveries of lactate anion from the initial solution, respectively. The relatively high percent recoveries for Dowex MWA-1 may be influenced by its ion-exchange capacity for lactate anion. Still higher recoveries should occur for both sorbents at higher $CO_2$ pressures.

EXAMPLE 3

Figure 3:
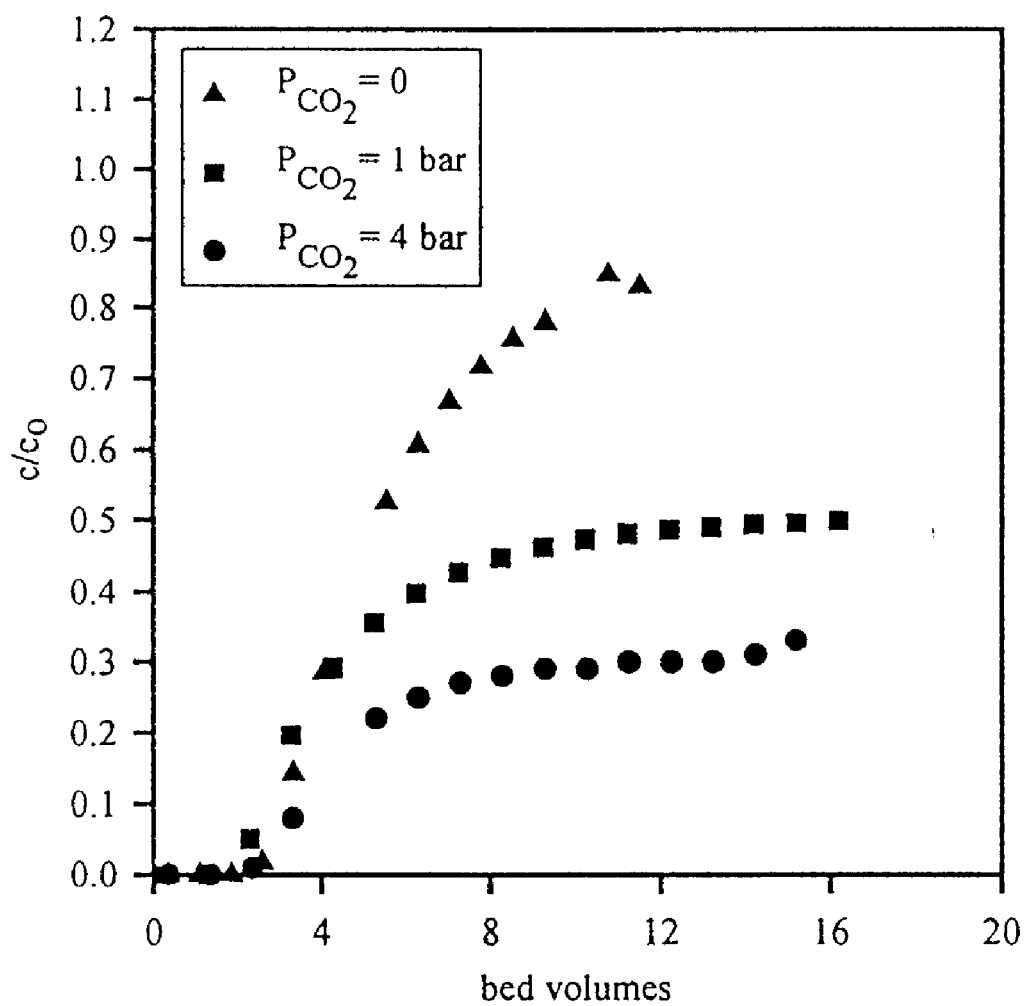
FIG. 3. Breakthrough curves for carbon dioxide-sustained fixed-bed adsorption of lactate anion onto Dowex MWA-1 at 25° C. The feed solutions were 0.05 M sodium lactate in equilibrium with carbon dioxide at several pressures.

Fixed-bed Adsorption of Lactic Acid Aided by Carbon Dioxide. FIG. 3 shows the breakthrough curves for carbon dioxide-sustained fixed-bed adsorption of lactate anion onto Dowex MWA-1 at 25° C. Lactate breakthrough curves were experimentally measured in the absence of $CO_2$ and at $CO_2$ pressures of 100 and 300 kPa gauge. Breakthrough of lactate anion occurs at about the same time for each experiment; however, a plateau in lactate concentration is reached for the solutions pressurized with $CO_2$. The plateaus suggest that about 50% and 70% of the lactate anions in the initial feed are removed by adsorption for $CO_2$ pressures of 100 and 300 kPa gauge, respectively. The locations of the plateaus at $c/c_o=0.5$ and $c/c_o=0.3$ for these two pressures are associated with the consumption of the hydrogen ions supplied by the reaction of $CO_2$ with water; the concentration of hydrogen ions generated at a pressure of 300 kPa is sufficient to protonate about 70% of the lactate anions in solution to produce lactic acid which is adsorbed. The remaining lactate anions remain in ionized form and cannot be recovered from solution by adsorption. Increasing the initial $CO_2$ pressure serves to increase the percent recovery of lactate anion by supplying additional hydrogen ions. In all cases, there would be a second breakthrough for lactate anion at some longer time, which would raise the effluent lactate anion concentration to its feed concentration (i.e., $c/c_o$ would approach a value of one). This second breakthrough would result from the sorbent bed reaching its equilibrium uptake capacity for lactic acid, based on the feed conditions. Still higher recoveries should occur for both sorbents at higher $CO_2$ pressures.

EXAMPLE 4

Figure 4:
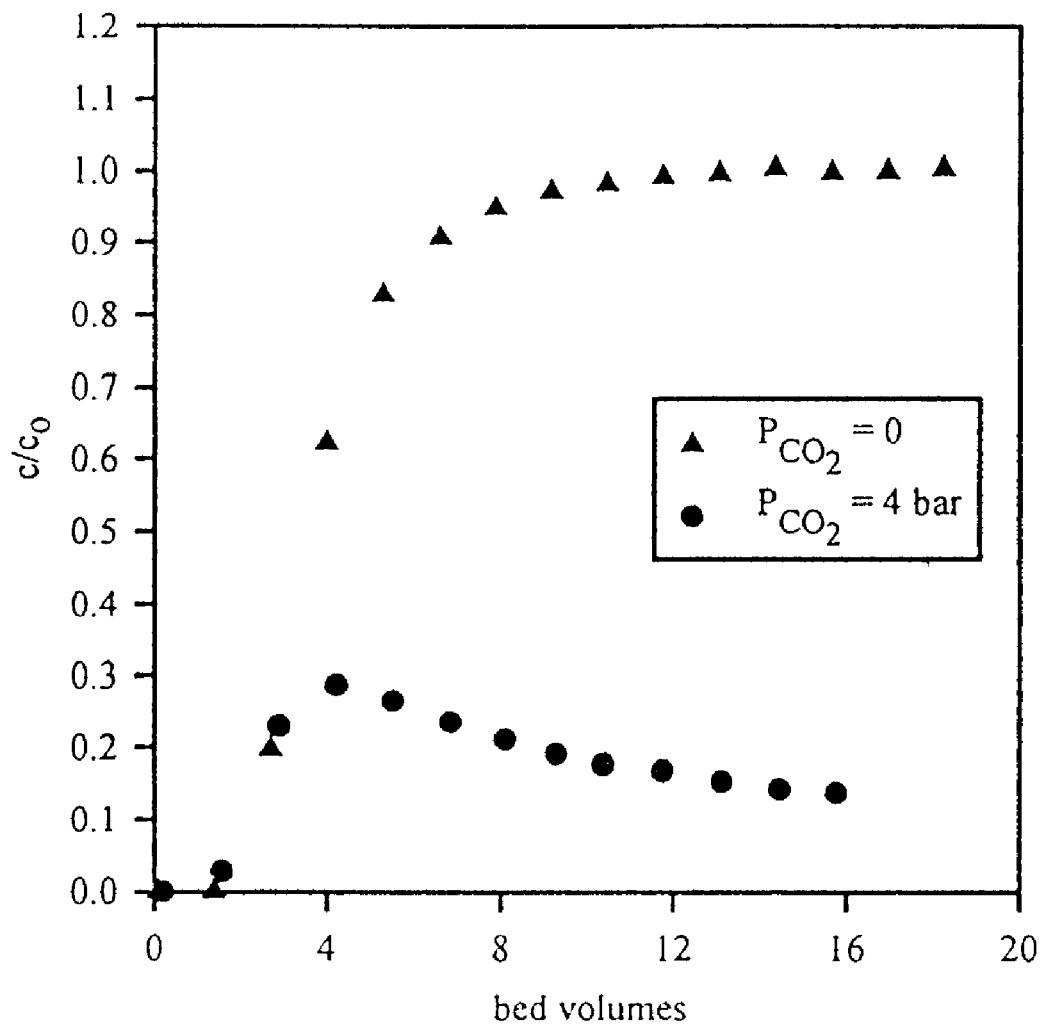
FIG. 4. Breakthrough curves for carbon dioxide-sustained fixed-bed adsorption of lactate anion onto Amberlite IRA-35 at 25° C. The feed solutions were 0.05 M sodium lactate in equilibrium with carbon dioxide at several pressures.

FIG. 4 shows the breakthrough curves for carbon dioxide-sustained fixed-bed adsorption of lactate anion onto Amberlite IRA-35 at 25° C. Lactate breakthrough curves were experimentally measured in the absence of $CO_2$ and at a $CO_2$ pressure of 300 kPa gauge. The concentration maximum in the lactate anion breakthrough curve for the pressurized case was an unexpected phenomenon.

One plausible explanation of the observed maximum in $c/c_o$ is a mass-transfer rate limitation for adsorption of lactic acid onto hard-to-reach sites within the polymer matrix of the sorbent. To test this explanation, the effect of volumetric flow rate on acid breakthrough was examined.

EXAMPLE 5

Figure 5:
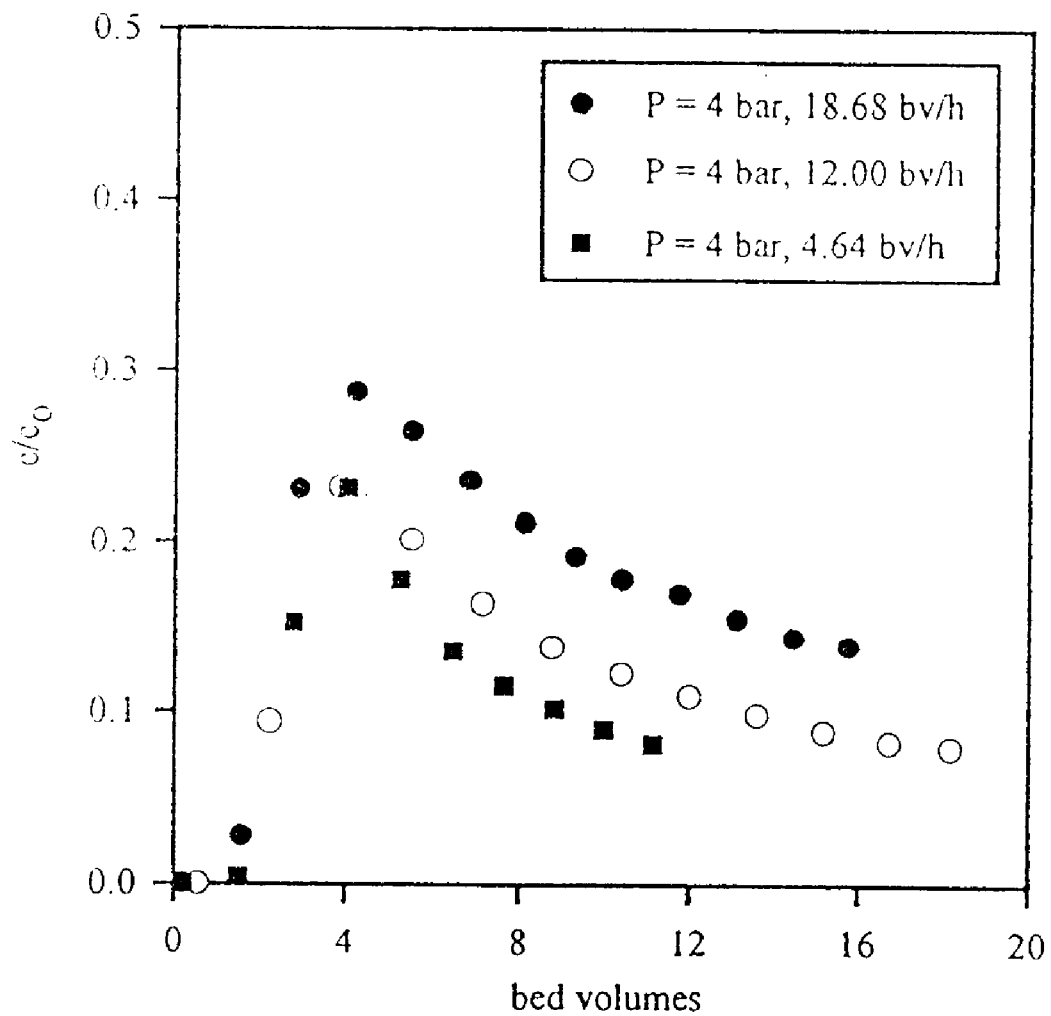
FIG. 5. Effect of volumetric flow rate on fixed-bed breakthrough of lactate anion during carbon dioxide-sustained adsorption onto Amberlite IRA-35 at 25° C.

FIG. 5 shows the breakthrough curves for lactate anion on Amberlite IRA-35 at volumetric flow rates of 4.64, 12.00, and 18.68 bed volumes per hour. All of the breakthrough curves rise through a maximum in $c/c_o$ between 4.0 and 4.5 bed volumes before gradually decreasing to a plateau value. As in FIG. 4, the plateau relates to the concentration of hydrogen ions available to protonate the amine sites of the sorbent. Decreasing the flow rate resulted in the equilibrium loading value being reached for a lesser number of bed volumes; however, it did not eliminate the maximum in $c/c_o$ under the conditions used. This result suggests that the rate of adsorption is limited by the mass-transfer rate of lactate anions to the hard-to-reach sites, but that this rate limitation alone cannot fully explain the maximum in $c/c_o$.

A second possible explanation for the maximum in $c/c_o$ is sorbent swelling. Initially, a fraction of the sorbent amine sites might be inaccessible to lactate anion. However, as the sorbent swells, these sites might become accessible to lactate anion, thereby increasing adsorption capacity and lowering the solution-phase lactate concentration.

Figure 6:
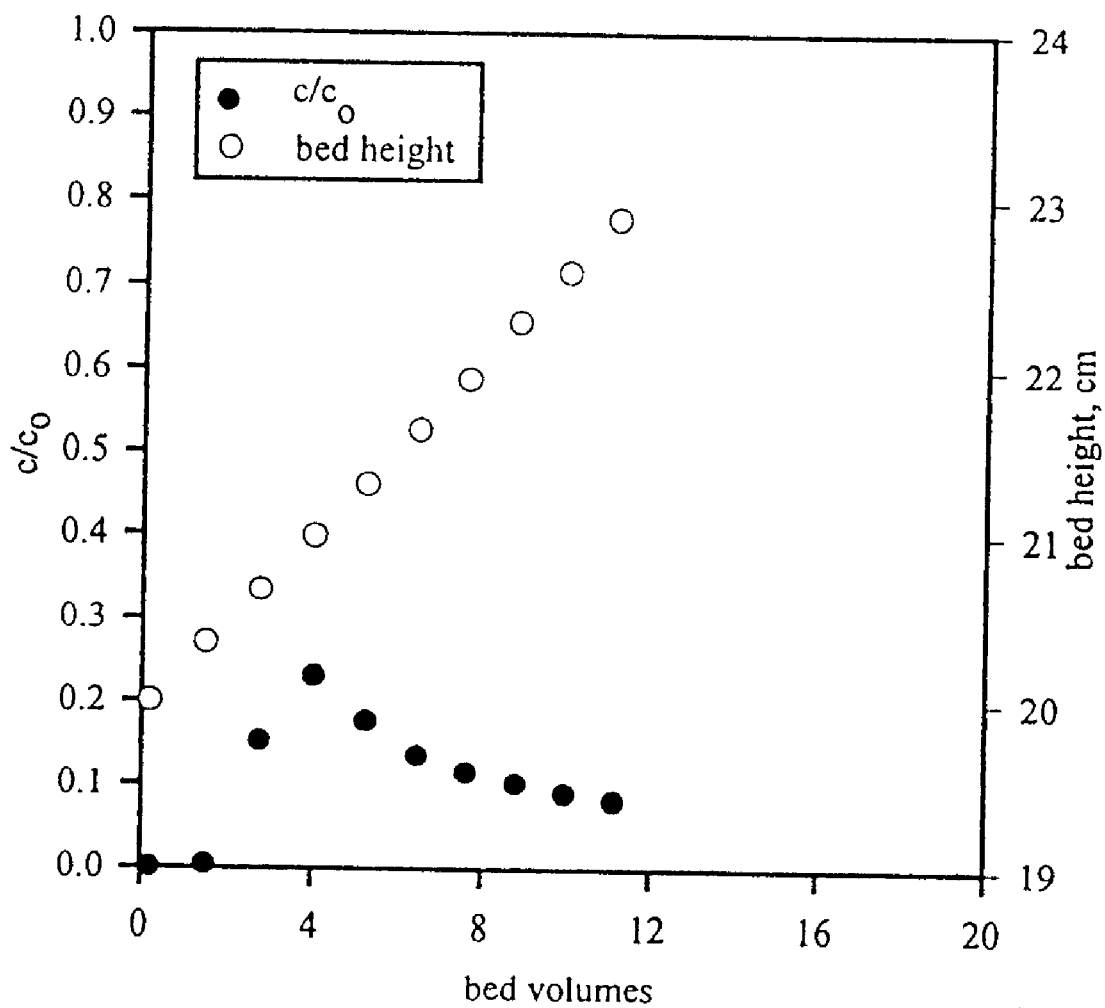
FIG. 6. Kinetics of sorbent bed expansion during carbon dioxide-sustained fixed-bed adsorption of lactate anion onto Amberlite IRA-35 at 25° C.

FIG. 6 shows the kinetics of the bed expansion for a volumetric flow rate of 4.64 bed volumes per hour. The expansion is linear with time over the course of the experiment. At about 10–12 bed volumes, it appears that the sorbent swelling has occurred sufficiently for lactate anion to access enough sites to achieve the plateau value associated with depletion of the available hydrogen ions. The maximum in $c/c_o$ therefore appears to result from the combined effects of a mass-transfer-limited rate of adsorption and swelling, which increases the fraction of accessible adsorption sites for lactate anion.

A further note is that the mechanisms postulated to explain the maximum in $c/c_o$ suggest that the effluent pH should go through a minimum over the same range of bed volumes associated with the maximum in effluent lactate anion concentration. Measured pH values over this range are, however, constant. To rationalize this result, we postulate that the hydrogen ion concentration is dictated by the sorbent basicity. Although a fraction of amine sites is initially inaccessible to lactate anion, these sites are accessible to hydrogen ions and, therefore, they are protonated. To maintain local charge neutrality, these sites may take up bicarbonate, rather than lactate. Thus, there is size-exclusion-based selectivity for uptake of bicarbonate over lactate on these sites. Once swelling has sufficiently occurred, lactate anion occupies some of the sites initially occupied by bicarbonate anion.

Both sorbents gave incomplete removal of lactate anion under the conditions used. These results indicate that a process to recover lactate anion would optimally operate at higher $CO_2$ pressures than those studied here and/or would recycle the lactate solution.

Figure 7:
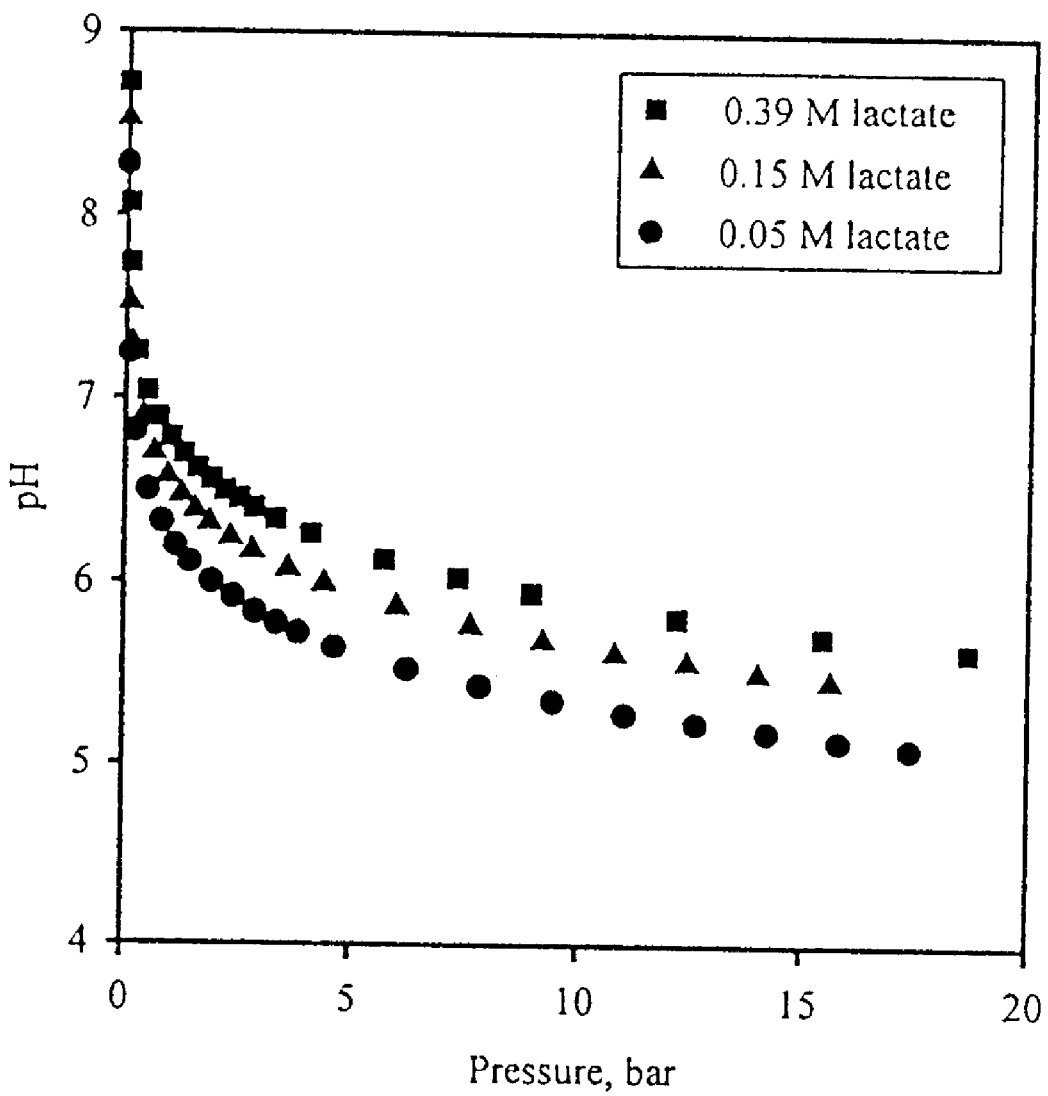
FIG. 7. Predicted pH profiles for carbon dioxide-sustained batch adsorption of lactate anion from aqueous solutions of 0.05, 0.15, and 0.39 M sodium lactate onto Dowex MWA-1 at 25° C.

FIG. 7 shows the predicted pH-pressure isotherms for adsorption of lactate anion from aqueous solutions of 0.05, 0.15 and 0.39 M sodium lactate onto Dowex MWA-1 at 25° C. The isotherms describe the equilibrium solution pH values over a range of equilibrium $CO_2$ pressures. With increasing $CO_2$ pressure, the equilibrium solution pH values decrease as expected. Working at a pressure of about 5 to 10 bar, the equilibrium pH values can be sustained at about pH=5.5–6, the range of pH values used for production of lactic acid by fermentation.

From the foregoing experiments and data derived therefrom, it can be seen that carbon dioxide can be used as an acidulent to sustain uptake capacity for adsorption of carboxylic acids at $pH>pK_a$ of the acid. The role of $CO_2$ is to supply protons to convert the carboxylate salt into its corresponding carboxylic acid. The resulting free acid is then removed from solution by sorption onto the basic sorbent.

What is claimed is:

1. In a process for recovering carboxylic acid from a carboxylic acid-containing aqueous feedstream wherein the feedstream is contacted with an acid-sorbing solid phase for a period of time sufficient to form an acid-depleted aqueous feedstream and an acid-enriched acid sorbing solid phase, and the acid-enriched acid-sorbing solid phase is subsequently treated to recover carboxylic acid therefrom, the improvement of carrying out the contact of said feedstream with said acid-sorbing solid phase in the presence of carbon dioxide under a pressure ranging from about 10 to about 2000 kPa gauge.

2. The process of claim 1 wherein said sorbent is a basic material.

3. The process of claim 2 wherein said basic material is a macroreticular polymeric sorbent.

4. The process of claim 3 wherein said sorbent is a styrene-divinylbenzene copolymer with primarily tertiary-amine and about 10% quaternary-amine groups.

5. The process of claim 3 wherein said sorbent is an acrylic-divinylbenzene with tertiary-amine groups.

6. The process of claim 1 wherein said carbon dioxide is maintained at a pressure ranging from about 100 to about 320 kPa gauge.

7. A process for recovering carboxylic acid from a carboxylic acid-containing aqueous feedstream comprising:
   a) contacting a carboxylic acid-containing feedstream with an acid-sorbing solid phase under conditions whereby carboxylic acid is sorbed from the feedstream to the acid-sorbing solid phase, thereby forming an acid-depleted aqueous feedstream and an acid-enriched acid-sorbing solid phase, the contacting of said carboxylic acid feedstream with said acid-sorbing solid phase being carried out in the presence of carbon dioxide under a pressure ranging from about 10 to about 2000 kPa gauge;
   b) separating the acid-depleted aqueous feedstream from the acid-enriched acid sorbing solid phase;
   c) contacting the separated acid-sorbing solid phase with an organic solution of low-molecular-weight alkylamine, thereby solubilizing said carboxylic acid from the sorbing solid phase into said organic solution as an alkylamine-carboxylic acid complex, and forming carboxylic-acid lean acid-sorbing phase;
   d) separating the organic solution of an alkylamine-carboxylic acid complex from the acid-lean acid-sorbing phase;
   e) treating the organic solution of an alkylamine-carboxylic acid complex to decompose the an alkylamine-carboxylic acid complex to yield the carboxylic acid and the alkylamine; and
   f) recovering the carboxylic acid yielded in step (e).

8. The process of claim 7 wherein in step (c) the alkylamine is a trialkylamine.

9. The process of claim 8 wherein the trialkylamine is trimethylamine.

10. The process of claim 7 wherein in step (e) said treating comprises removing the organic solvent and alkylamine.

11. The process of claim 7 wherein said sorbent is a basic material.

12. The process of claim 11 wherein said basic material is a macroreticular polymeric sorbent.

13. The process if claim 12 wherein said polymeric sorbent is a styrene-divinylbenzene copolymer with primarily tertiary-amine groups and about 10% quaternary-amine groups.

14. The process of claim 12 wherein said polymeric sorbent is an acrylic-divinylbenzene with tertiary-amine groups.

15. The process of claim 7 wherein the carbon dioxide is under a pressure ranging from about 100 to about 320 kPa gauge.

16. A process for recovering carboxylic acid from a carboxylic acid-containing aqueous feedstream comprising:
   a) contacting a carboxylic acid-containing feedstream with an acid-sorbing solid phase under conditions whereby carboxylic acid is sorbed from the feedstream to the acid-sorbing solid phase, thereby forming an acid-depleted aqueous feedstream and an acid-enriched acid-sorbing solid phase, the contacting of said carboxylic acid feedstream with said acid-sorbing solid phase being carried out in the presence of carbon dioxide under a pressure ranging from about 10 to about 2000 kPa gauge;
   b) separating the acid-depleted aqueous feedstream from the acid-enriched acid sorbing solid phase; and
   c) recovering free carboxylic acid from the acid-enriched acid sorbing solid phase.

* * * * *